United States Patent
Bakhru et al.

(10) Patent No.: US 9,956,287 B2
(45) Date of Patent: May 1, 2018

(54) STABLE GLUCAGON FORMULATIONS

(71) Applicant: Perosphere Inc., Danbury, CT (US)

(72) Inventors: Sasha H. Bakhru, Danbury, CT (US);
Bryan E. Laulicht, Danbury, CT (US);
Xuan Jiang, Danbury, CT (US);
Lirong Chen, Danbury, CT (US);
Solomon S. Steiner, Danbury, CT (US)

(73) Assignee: Perosphere Inc., Danbury, CT (US)

( * ) Notice: Subject to any disclaimer, the term of this patent is extended or adjusted under 35 U.S.C. 154(b) by 0 days. days.

(21) Appl. No.: 14/766,347

(22) PCT Filed: Feb. 6, 2014

(86) PCT No.: PCT/US2014/015030
§ 371 (c)(1),
(2) Date: Aug. 6, 2015

(87) PCT Pub. No.: WO2014/124096
PCT Pub. Date: Aug. 14, 2014

(65) Prior Publication Data
US 2015/0374825 A1    Dec. 31, 2015

Related U.S. Application Data

(60) Provisional application No. 61/761,545, filed on Feb. 6, 2013, provisional application No. 61/875,904, filed on Sep. 10, 2013.

(51) Int. Cl.
*A61K 9/08* (2006.01)
*A61K 47/10* (2017.01)
*A61K 38/26* (2006.01)
*A61K 9/00* (2006.01)
*A61K 47/22* (2006.01)
*A61K 47/26* (2006.01)
*A61K 38/00* (2006.01)

(52) U.S. Cl.
CPC ............ *A61K 47/10* (2013.01); *A61K 9/0019* (2013.01); *A61K 38/26* (2013.01); *A61K 47/22* (2013.01); *A61K 47/26* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 2005/0008661 A1* | 1/2005 | Fereira | A61K 47/32 424/400 |
| 2010/0190706 A1 | 7/2010 | Bjerregaardjensen | |
| 2011/0237510 A1 | 9/2011 | Steiner | |
| 2012/0232001 A1 | 9/2012 | Prestrelski | |

FOREIGN PATENT DOCUMENTS

WO    9800152    1/1998

OTHER PUBLICATIONS

Arakawa et al., "Biotechnology applications of amino acids in protein purification and formulations," Amino Acids 33:587-605 (2007).*
International Search Report and Written Opinion for corresponding PCT application PCT/US2014/015030 dated Jul. 16, 2014.
International Preliminary Report on Patentability for corresponding PCT application PCT/US2014/015030 dated Aug. 20, 2015.

* cited by examiner

Primary Examiner — Julie Ha
Assistant Examiner — Kristina M Hellman
(74) Attorney, Agent, or Firm — Pabst Patent Group LLP

(57) ABSTRACT

Stabilized formulations containing a peptide, such as a glucagon, are described herein. The formulations are in the form of a solution or suspension, which exhibit little or no chemical degradation and/or aggregation of the peptide over an extended period of time. In some embodiments, the formulations are in the form of a solution containing the peptide, a solvent such as glycerin, and one or more thermal stabilizers. In other embodiments, the formulation is in the form of a suspension containing nano- and/or microparticles containing the peptide suspended in a non-aqueous, non-solvent. The nano- and/or microparticles can be prepared by micronizing the peptide with one or more humectants, such as salts, sugars, water-soluble polymers, and combinations thereof which increase the rate of dissolution of the peptide upon administration.

36 Claims, 1 Drawing Sheet

STABLE GLUCAGON FORMULATIONS

CROSS-REFERENCE TO RELATED APPLICATIONS

This application is a 371 application of International Application No. PCT/US2014/015030, filed Feb. 6, 2014, which claims priority to U.S. Provisional Application No. 61/761,545, filed on Feb. 6, 2013 and U.S. Provisional Application No. 61/875,904, filed on Sep. 10, 2013.

FIELD OF THE INVENTION

This invention is in the field of stabilized peptide solutions and suspensions, particularly stabilized glucagon solutions and suspensions.

BACKGROUND OF THE INVENTION

Glucagon, as with most therapeutic peptides and proteins, is thermally unstable. In aqueous solution, glucagon both degrades and begins to form aggregates within hours at room temperature. As a result, glucagon must be stored as a lyophilized powder that requires storage under controlled conditions of temperature and humidity. Lyophilized glucagon for injection is a 29 amino acid synthetic peptide hormone commercially available in a kit including diluent for resuspension, and is marketed as GlucaGen® HypoKit by Novo Nordisk and by Eli Lilly. The diluent for 1 mg of lyophilized glucagon contains 12 mg/mL glycerin, water for injection, and hydrochloric acid to adjust to pH ~2.

The lyophilized glucagon must be reconstituted with a diluent prior to its use, such as emergency cases of diabetic hypoglycemia. This delays treatment. Also, since the formulation must be stored at 20-25° C., the patient cannot carry it with them. This still further delays treatment.

The thermal, chemical, and physical instability of lyophilized and aqueous glucagon also prohibit current formulations from inclusion in pump-based therapies, where the pump is kept on the patient (i.e., temperature >25° C.), which could otherwise offer enhanced treatment for diabetic patients.

There is a longstanding, unmet clinical need for a pre-constituted, thermally, chemically, and physically stable glucagon formulation.

Therefore, it is an object of the invention to provide pre-constituted, thermally, chemically, and physically stable glucagon formulations and methods of making and using thereof.

SUMMARY OF THE INVENTION

Stabilized formulations containing a peptide, such as a glucagon, or a combination of peptides are described herein. The formulations are in the form of a solution or suspension, which exhibit little or no chemical degradation and/or aggregation of the peptide over an extended period of time. In some embodiments, the formulations are in the form of a solution containing the peptide, a solvent such as glycerin, in the presence or absence of a co-solvent such as ethanol, and one or more thermal stabilizing excipients. In a particular embodiment, the formulation is a solution containing (1) glycerol, (2) from about 5 to about 100 mg/ml of a stabilizing agent (e.g. a di-arginine piperazine), preferably about 20 mg/ml of a di-arginine piperazine, (3) from about 5 to about 15 mg/ml of a pH-adjusting agent (e.g., sodium bicarbonate), preferably about 10 mg/ml sodium bicarbonate, to achieve a pH of about 6-8.5, preferably about 8 (4) from about 5 to about 15 mg/ml of a sugar (e.g., sucrose), preferably about 10 mg/ml sucrose, and (5) from about 0.5 to about 3.0 mg/ml of an antimicrobial agent (e.g., m-cresol), preferably about 2 mg/ml m-cresol. In a particular embodiment, the concentration of m-cresol is 1.5 mg/ml. The concentrations throughout the application refer to amount of component (e.g., peptide, thermal stabilizer, etc.) per ml of non-solvent (e.g., glycerin).

In other embodiments, the formulation is in the form of a suspension containing nano- and/or microparticles containing the peptide suspended in a non-aqueous, non-solvent. The nano- and/or microparticles can be prepared by micronizing the peptide with one or more humectants, such as salts, sugars, water-soluble polymers, and combinations thereof which increase the rate of dissolution of the peptide upon administration.

DETAILED DESCRIPTION OF THE INVENTION

I. Definitions

Figure 1:
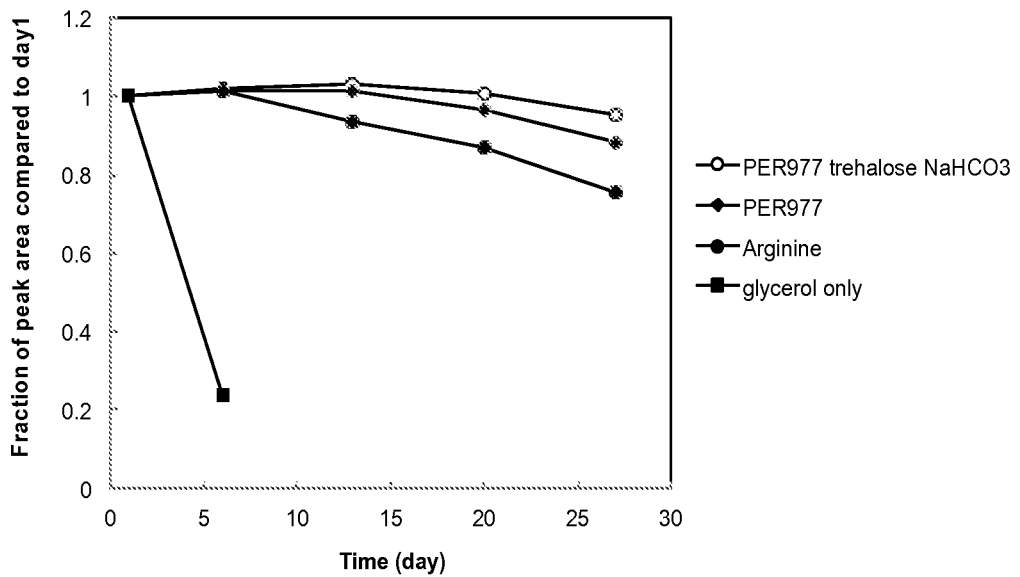
FIG. 1 is a graph showing the reduction in the peak area of the glucagon peak as measured by HPLC as a function of time (days) for glucagon dissolved in glycerin (■), glucagon dissolved in glycerin with arginine (●), glucagon dissolved in glycerin with the di-arginine piperazine PER977 (♦), and glucagon dissolved in glycerin with the di-arginine piperazine PER977, trehalose, and sodium bicarbonate (o), when stored at 40° C.

"Stable" as used herein, means a less than 20, 19, 18, 17, 16, 15, 14, 13, 12, 11, 10, 9, 8, 7, 6, 5, 4, 3, 2, or 1 percent reduction of the peak area of the glucagon peak as measured by HPLC over a period of at least about 5, 7, 10, 14, 15, 21, 25, 28, 30, 35, 40, 45, or 50 days at a temperature of at least about 25 degrees Celsius. "Stable" can be used to refer to chemical degradation, i.e., changes in the chemical structure of peptide being administered, or physical degradation, i.e., changes in the physical properties, for example, due to aggregation. For example, glucagon is known to exhibit chemical instability (degradation of the peptide) and physical instability (aggregation of the peptide) in aqueous solvents. These phenomena are observed at room temperature (e.g., 25° C.) but are more pronounced at temperatures above room temperature, such as body temperature (e.g., ~37° C.).

As used herein, "glucagon" refers to the full-length peptide, glucagon. "GLP-1" refers to glucagon-like peptides (GLP-1, amino acids 7-36 amide and 7-37), and analogs and derivatives thereof, unless otherwise specified.

As used herein, a "sugar" refers to a monosaccharide or disaccharide. Saccharides can exist as a straight chain or cyclic conformation. Preferred examples include sucrose, trehalose, dextrose, lactose, maltose, and galactose.

As used herein, "osmolarity" is the concentration of a solution in terms of milliosmoles of solutes per liter of solution. The normal plasma osmolarity is in the range of 280-310 mOs/kg.

As used herein, "physiological pH" is in the range of 6.8 to 7.5, preferably 7 to 7.4.

The term "parenteral injection" refers to the administration of therapeutic agents, such as peptide compounds, via injection under or through one or more layers of skin or mucus membranes of an animal, such as a human. Standard parenteral injections are given into the subcutaneous or intramuscular region of an animal, e.g., a human patient. These deep locations are targeted because the tissue expands more easily, relative to shallow dermal sites, to accommodate the injection volumes required to deliver most therapeutic agents.

As used herein, "physiological temperature" is between about 30 and 37° C.

The term "pharmaceutically acceptable carrier" means a pharmaceutically acceptable solvent, suspending agent or vehicle for delivering a compound of the present invention to the animal or human. The carrier is typically a liquid.

The term "pharmaceutically acceptable" ingredient, diluent, excipient or component is one that is suitable for use with humans and/or animals without undue adverse side effects (e.g., such as significant toxicity, irritation, and allergic response).

The term "diameter" is art-recognized and is used herein to refer to either of the physical diameter or the hydrodynamic diameter. The diameter of an essentially spherical particle may refer to the physical or hydrodynamic diameter. The diameter of a nonspherical particle may refer preferentially to the hydrodynamic diameter. As used herein, the diameter of a non-spherical particle may refer to the largest linear distance between two points on the surface of the particle. When referring to multiple particles, the diameter of the particles typically refers to the average diameter of the particles. Particle diameter can be measured using a variety of techniques in the art including, but not limited to, dynamic light scattering.

The term "microparticles" is art-recognized, and includes particles or spheres having a size ranging from about one or greater up to about 1000 microns. A microparticle may be spherical or nonspherical and may have any regular or irregular shape. If the structures are less than about one micron in diameter, then the corresponding art-recognized term "nanoparticle" may be utilized. In certain embodiments, the nanoparticles have an average diameter of less than about 1000 nm, 500 nm, 200 nm, 100 nm, 50 nm, 10 nm, or 1 nm. In some embodiments, the particles have a diameter from about 10-500 nm, preferably from 100-500 nm, more preferably 250-500 nm.

A composition containing microparticles or nanoparticles may include particles of a range of particle sizes. In certain embodiments, the particle size distribution may be uniform, e.g., within less than about a 20% standard deviation of the mean volume diameter, and in other embodiments, still more uniform, e.g., within about 10% of the median volume diameter.

The phrases "parenteral administration" and "administered parenterally" are art-recognized terms, and include modes of administration other than enteral and topical administration, such as injections, and include without limitation intravenous, intramuscular, intrapleural, intravascular, intrapericardial, intraarterial, intrathecal, intracapsular, intraorbital, intracardiac, intradennal, intraperitoneal, transtracheal, subcutaneous, subcuticular, intraarticular, subcapsular, subarachnoid, intraspinal and intrastemal injection and infusion.

The term "non-solvent" as used herein refers to solvents that achieve less than about 0.1 mg/mL solubility of the desired solute at about 25 degrees Celsius.

"Aromatic", as used herein, refers to 5-12-membered, preferably 5-, 6- and 7-membered aromatic, heterocyclic, fused aromatic, fused heterocyclic, biaromatic, or biheterocyclic ring systems, optionally substituted. Broadly defined, "Ar", as used herein, includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF3, —CN, or the like. The term "Ar" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, (Cl-4)alkyl, phenyl or benzyl, and optionally containing 1-3 double bonds and optionally substituted with one or more substituents. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

II. Formulations

Stabilized formulations containing a peptide, such as a glucagon, are described herein. The formulations are in the form of a solution or suspension, which exhibit little or no chemical degradation and/or aggregation of the peptide over an extended period of time. In some embodiments, the formulations are in the form of a solution containing the peptide, a solvent such as glycerin, and one or more thermal stabilizing excipients. The formulation can contain additional excipients including, but not limited to, sugars, pH-adjusting agents, antimicrobial agents, and combinations thereof. In other embodiments, the formulation is in the form of a suspension containing nano- and/or microparticles containing the peptide suspended in a non-aqueous, non-solvent. The nano- and/or microparticles can be prepared by micronizing the peptide with one or more humectants, such as salts, sugars, water-soluble polymers, and combinations thereof which increase the rate of dissolution of the peptide upon administration.

In one embodiment, the formulation contains a peptide, such as a glucagon, dissolved in a non-aqueous solvent, such as glycerin to form a solution.

In another embodiment, a peptide, such as a glucagon, is dissolved in a non-aqueous solvent, such as glycerin, to form a solution and an amino acid, such as L-arginine, L-ornithine, L-lysine, and/or L-histidine is added to the solution to improve the thermal stability of the solution.

In another embodiment, a peptide, such as a glucagon, is dissolved in a non-aqueous solvent, such as glycerin, to form a solution and a compound of Formula I, such as PER977 or di-arginine piperazine, is added to the solution to improve the thermal stability of the solution.

In still another embodiment, a peptide, such as a glucagon, is dissolved in a non-aqueous solvent, such as glycerin, to form a solution and a compound of Formula I, such as DAP, a sugar, such as a trehalose or sucrose, and a pH-adjusting agent, such as sodium bicarbonate is added to the solution to improve the thermal stability of the peptide. The formulations can further contain an antimicrobial agent (e.g., m-cresol), which can also act as a stabilizing agent.

In still another embodiment, a peptide, such as glucagon, is dissolved in a combination of non-aqueous solvents, such as glycerin and ethanol, to form a solution and a compound of Formula I, such as DAP, a sugar, such as trehalose or sucrose, and a pH-adjusting agent, such as sodium bicarbonate, is added to the solution to improve thermal stability of the peptide. Ethanol can be added to reduce the viscosity of glycerin to improve injectability. In specific embodiments the co-solvent system contains from about 1 to about 50, preferably from about 10 to about 40, more preferably from about 20 to about 30 volume percent ethanol in glycerin. The formulation can further contain an antimicrobial agent (e.g., m-cresol), which can also act as a stabilizing agent.

A. Peptides

The stable formulations described herein contain one or more peptides, or salts, analogs, and/or mixtures thereof. Exemplary peptides include, but are not limited to, glucagon, pramlintide, insulin, leuprolide, an luteinizing-hormone-releasing hormone (LHRH) agonist, parathyroid hormone (PTH) or its pharmaceutically active sub-units, amylin, botulinum toxin, hematide, an amyloid peptide, cholecystikinin, gastric inhibitory peptide, an insulin-like growth factor, growth hormone releasing factor, anti-microbial factor, glatiramer, glucagon-like peptide-1 (GLP-1), a GLP-1 agonist, e.g., exenatide, interferons, insulin, insulin analogs, c-peptide, amylin, analogs thereof, and mixtures thereof.

In a particular embodiment, the peptide is glucagon or a glucagon analog or peptidomimetic, or a salt thereof. Glucagon is synthesized in the pancreas. It is a highly conserved polypeptide containing a single chain of 29 amino acids, with a molecular weight of 3485 Daltons. Recombinant glucagon can be expressed in *E. coli* and purified to at least 98% pure prior to use. Proteolytic removal of the amino-terminal histidine residue leads to loss of the biological activity. Glucagon has a helical conformation in the crystalline state, while in dilute aqueous solutions it has a random coil conformation with 15% alpha helix at the C-terminal end. In other embodiments, the peptide is glucagon-like peptide-1 (GLP-1) or a GLP-1 analog or agonist (e.g., exenatide).

The dosage administered is dependent upon a variety of factors, such as the pharmacodynamic characteristics of the particular peptide, salt, or combination thereof; the age, health, or weight of the subject; the nature and extent of symptoms; the metabolic characteristics of the therapeutic agent and patient, the kind of concurrent treatment; the frequency of treatment; or the effect desired. The appropriate dosage can be readily determined by the attending physician.

Generally, the peptide is present in the formulation in an amount ranging from about 0.5 mg/mL glucagon to about 100 mg/mL glucagon (e.g., about 0.5, 1, 2, 3, 4, 5, 6, 7, 8, 9, 10, 15, 20, 25, 30, 35, 40, 45, 50, 55, 60, 65, 70, 75, 80, 85, 90, 95, or 100 mg/mL glucagon) in a pharmaceutically acceptable non-aqueous solvent, in some embodiments the non-aqueous solvent is glycerin. In some embodiments, the peptide is present in the formulation in an amount ranging from about 0.5 mg/mL glucagon to about 60 mg/mL glucagon, from about 1 mg/mL glucagon to about 20 mg/mL glucagon, or from about 1 mg/mL glycerin to about 5 mg/mL glucagon. In other embodiments, the peptide is present in the formulation in an amount ranging from about 1 mg/mL glucagon to about 10 mg/mL glucagon. In yet other embodiments, the peptide is present in the formulation in an amount ranging from about 0.5 mg/mL glucagon to about 5 mg/mL glucagon.

B. Solvent

The formulations described herein can be in the form of a solution or a suspension. In those embodiments wherein the formulation is a solution, the peptide is dissolved in a non-aqueous, non-solvent. "Non-aqueous", as used herein, means less than 5%, 4%, 3%, 2%, 1%, 0.9%, 0.8%, 0.7%, 0.6%, 0.5%, 0.4%, 0.3%, 0.2%, or 0.1% water by weight of the formulation. Exemplary non-aqueous, non-solvents include, but are not limited to, glycerin, low-molecular weight polyethylene glycol, ethylene glycol, propylene glycol, alcohols such as ethanol, and combinations thereof "Low-molecular weight", as used herein, generally means a weight average molecular weight from about 200 to about 600 Daltons.

In other embodiments, the formulation is in the form of a suspension, wherein the peptide is suspended in a non-aqueous, inert carrier. Glucagon solutions in water, water mixed with water-miscible organic solvents, and DMSO can be prepared prior to micronization. Once the peptide has been micronized, it can be suspended in a pharmaceutically carrier for administration to a patient. Exemplary carriers include, but are not limited to, glycerin, low-molecular weight polyethylene glycol, ethylene glycol, propylene glycol, alcohols such as ethanol, and combinations thereof "Low-molecular weight", as used herein, generally means a weight average molecular weight from about 200 to about 600 Daltons.

In one embodiment, the solvent is glycerin in combination with ethanol as a cosolvent, wherein the concentration of ethanol is from about 10 to about 50, preferably from about 10 to about 40, more preferably from about 20 to about 30 volume percent ethanol in glycerin.

C. Stabilizers for Solutions

The formulations described herein can further contain one or more compounds, which further stabilize the peptide in solution or suspension to decrease or prevent chemical degradation and/or physical instability (e.g., aggregation). In some embodiments, the one or more stabilizers improve the thermal stability of peptide solutions, such as glucagon solutions. This allows for the storage of the solutions over an extended period of time with little or no chemical degradation and/or physical instability and eliminates the need for reconstitution of lyophilized powders of the peptide immediately before use.

In those embodiments wherein the formulation is a solution, the stabilizer can be an amino acid, a pH-adjusting agent, a sugar, a stabilizer of Formula I (shown below), or combinations thereof.

Suitable amino acids that can be used to stabilize the peptide in solution or suspension, particularly in solution, include, but are not limited to, basic amino acids, such as L-arginine, ornithine, and histadine.

Suitable sugars include, but are not limited to, trehalose, dextrose, maltose, sucrose, and galactose. In one embodiment, the formulation contains sucrose in a concentration from about 1 mg/ml sucrose to about 50 mg/ml sucrose, preferably about 10 mg/ml sucrose. In one embodiment, the formulation contains trehalose in a concentration from about 1 mg/ml trehalose to about 50 mg/ml trehalose, preferably about 10 mg/ml trehalose.

Suitable pH-adjusting agents include organic and inorganic acids and bases. Exemplary bases include, but are not limited to, sodium bicarbonate, hydroxides, citrates, EDTA, and carbonates. In one embodiment, the formulation contains sodium bicarbonate in a concentration from about 1 mg/ml sodium bicarbonate to about 50 mg/ml sodium bicarbonate, preferably about 10 mg/ml sodium bicarbonate. In one embodiment, the concentration is 20 mg/ml sodium bicarbonate. In some preferred embodiments, sodium bicarbonate is added in an amount to adjust the pH to within a range of 7.5 to 9, more preferably to within a range of 8 to 8.5, most preferably to within a range of 8 to 8.25.

The stabilizer can also be a compound of Formula I:

Y-M-X-L-A-L'-X'-M'-Y'    Formula I wherein:

A is a substituted or unsubstituted aromatic or non-aromatic, carbocyclic or heterocyclic ring or a linear moiety;

L and L' are the same or different and are linkers;

X and X' are the same or different and are absent or are a functional group that attaches the linker L to M;

M and M' are the same or different and are absent or is a linker than attaches X to Y; and Y and Y' are the same or different and are a moiety containing one or more cationic atoms or groups or one or more groups that become cationic under physiological conditions. Examples include amine and guanidine moieties as well as phosphorous containing moieties, such as alkyltriphenylphosphonium, tetraphenylphosphonium, tetraphenylarsonium, tribenzyl ammonium, and phosphonium moieties. Additional cationic moieties include cationic oligomers and polymers, such as oligo- or polylysine, oligo- or polyarginine, and N-alkylated polyethylene imine. Other cationic moieties include delocalized lipophilic cations containing one to three carbimino, sulfimino, or phosphinimino units.

The compounds can be symmetrical or asymmetrical; that is, one or more of L, L', X, X', M, M', Y, or Y' can be the same or different. The compounds can be chiral (i.e., contain one or more chiral centers) or achiral.

In some embodiments, A is a heterocyclic moiety. In other embodiments, A is a heterocyclic moiety and L and L' are a substituted or unsubstituted alkylene chain. In still other embodiments, A is a heterocyclic moiety, L and L' are a substituted or unsubstituted alkylene chain, and X and X' are —NH—C(=O)—. In still other embodiments, A is a heterocyclic moiety, L and L' are a substituted or unsubstituted alkylene chain, X and X' are —NH—C(=O)—, and M and M' are a substituted alkylene chain. In still other embodiments, A is a heterocyclic moiety, L and L' are a substituted or unsubstituted alkylene chain, X is —NH—C(=O)—, M and M' are a substituted alkylene chain, and Y and Y' are a guanidine moiety. In particular embodiments, A is a 1,4 or 2,5 disubstituted piperazine ring.

In the preferred embodiment, the compound is di-arginine piperazine (DAP). The chemical structure of DAP (a) and a related compound (b) are:

a)

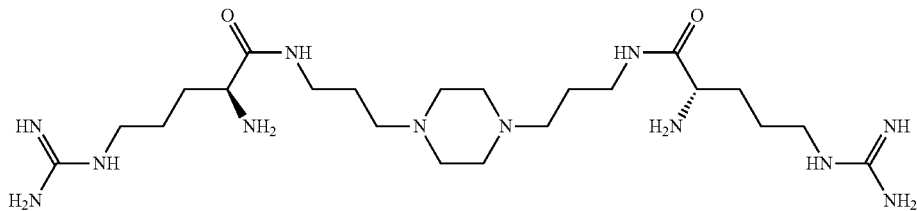

2-Amino-5-guanidino-pentanoic acid (3-{4-[3-(2-amino-5-guanidino-pentanoylamino)-
propyl]-piperazin-1-yl}-propyl)-amide b)

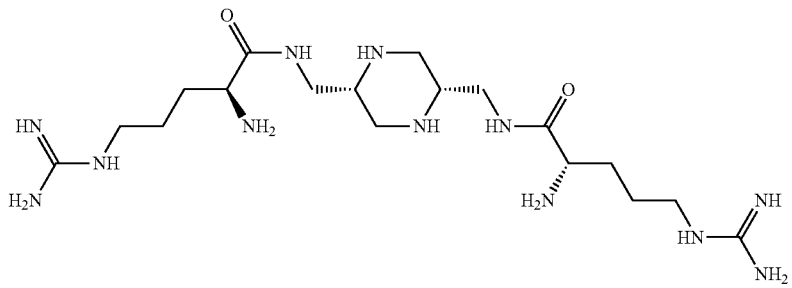

2-Amino-5-guanidino-pentanoic acid {5-[(2-amino-5-guanidino-pentanoylamino)-methyl]-
piperazin-2-ylmethyl}-amide As shown in the Examples, the addition of an amino acid alone, such as arginine, significantly improves the stability of glucagon solutions in glycerin compared to glucagon in glycerin alone. However, the substitution of arginine with PER977, alone or in combination with trehalose and sodium bicarbonate, improves the thermal stability of the glucagon solution over a period of 30 days, as shown in FIG. 1.

In some embodiments, the concentration of PER977 is from about 5 mg/ml PER977 to about 100 mg/ml PER977, preferably about 10 mg/ml to 50 mg/ml PER977. In one embodiment, the concentration is about 10 mg/ml PER977. In another embodiment, the concentration is about 20 mg/ml PER977.

D. Excipients for Suspensions

In other embodiments, the peptide, such as glucagon, is suspended in a non-aqueous, inert carrier. Suitable carriers include, but are not limited to, low-molecular weight polyethylene glycol ethylene glycol, propylene glycol, alcohols, such as ethanol, and combinations thereof "Low-molecular weight", as used herein, generally means a weight average molecular weight from about 200 to about 600 Daltons.

In order to increase the speed of dissolution of the peptide after injection, the peptide can be micronized with one or more humectants to prepare nano- and/or microparticles of the peptide. Suitable humectants include, but are not limited to, salts, such as sodium chloride, calcium chloride, potassium chloride, magnesium chloride, metal salts of oleates and stearates, sugars such as trehalose, dextrose, lactose, maltose, and galactose, and water-soluble polymers, such as polyethylene glycols (MW>1 kDa), chitosan, polyvinyl alcohol, and polyamino acids such as polyornithine, polyarginine, polylysine.

E. Other Additives, Excipients

The solutions and/or suspensions described herein can contain one or more excipients in addition to the thermal stabilizers and humectants described above. Suitable excipients include surfactants, including ionic and non-ionic surfactants, preservative, such as EDTA, sodium benzoate, metacresol, and benzyl alcohol, benzalkonium chloride, methyl- or propyl-paraben, or chlorobutanol, potassium sorbate, sorbic acid, ethyl vanillin, phenol, and parachlorophenol, and antioxidizing agents, such as sodium bisulfite, sodium sulfite, ascorbic acid or methionine, either alone or in combination, osmolarity adjusting agents such as salts and sugars, and pH adjusting agents both of which are listed above. In some embodiments, the formulation contains m-cresol. In one embodiment, the formulation contains m-cresol in a concentration from about 0.5 mg/ml m-cresol to about 3.0 mg/ml m-cresol, preferably about 2 mg/ml m-cresol. In one embodiment, the concentration is about 2 mg/ml m-cresol. In another embodiment, the concentration is about 1.5 mg/ml m-cresol.

Surfactants can be incorporated into the formulations to aid in the flow of the formulation through the needle of the injection device and/or to aid in the dissolution of the solid suspended in a vehicle upon administration. Exemplary surfactants include anionic surfactants, cationic surfactants, amphoteric (amphipathic/Amphiphilic) surfactants, and nonionic surfactants.

Suitable anionic surfactants include, for example, monovalent alkyl carboxylates, acyl lactylates, alkyl ether carboxylates, N-acyl sarcosinates, polyvalent alkyl carbonates, N-acyl glutamates, fatty acid-polypeptide condensates, sulfuric acid esters, alkyl sulfates, such as sodium lauryl sulfate (SLS), ethoxylated alkyl sulfates, ester linked sulfonates, alpha olefin sulfonates, and phosphated ethoxylated alcohols.

Suitable cationic surfactants include, for example, monoalkyl quaternary ammonium salts, dialkyl quaternary ammonium compounds, amidoamines, and aminimides. Suitable amphoteric (amphipathic/amphophilic) surfactants, include, for example, N-substituted alkyl amides, N-alkyl betaines, sulfobetaines, and N-alkyl beta-aminoproprionates.

Suitable wetting (solubilizing) agents include nonionic surfactants such as, for example, polyoxyethylene compounds, ethoxylated alcohols, ethoxylated esters, ethoxylated amides, polyoxypropylene compounds, propoxylated alcohols, ethoxylated/propoxylated block polymers, and propoxylated esters, alkanolamides, amine oxides, fatty acid esters of polyhydric alcohols, ethylene glycol esters, diethylene glycol esters, propylene glycol esters, glyceryl esters, polyglyceryl fatty acid esters, sorbitan esters, sucrose esters, and glucose (dextrose) esters.

In one embodiment, the solution or suspension contains the antimicrobial agent metacresol.

III. Methods of Making

A. Solutions

The solutions can be prepared using a variety of techniques. In one embodiment, the one or more excipients, such as one or more thermal stabilizers, are dissolved in the non-aqueous solvent, e.g., glycerin. Once the excipients are dissolved, the peptide, e.g., glucagon, is dissolved in the non-aqueous solvent. Glucagon requires hours to days to dissolve in glycerin, which is likely the reason that glycerin has not been explored for use in commercial formulations. Once the solution is prepared, it can be stored in a syringe over extended periods of time, e.g., at least about 5, 7, 10, 14, 15, 21, 25, 28, or 30 days. The solutions are chemically and physically stable. For example, the solutions exhibit less than a 20, 19, 18, 17, 16, 15, 14, 13, 12, 11, 10, 9, 8, 7, 6, 5, 4, 3, 2, or 1 percent reduction of the peak area of the glucagon peak as measured by HPLC over a period of 5, 7, 10, 14, 15, 21, 25, 28, 30, 35, 40, 45, or 50 days. The fact that the solution can be stored in the device used for administration allows for expedited administration in rescue situations since the glucagon does not need to be reconstituted prior to use as required with formulations currently on the market. This is particularly important if the patient would have difficulty in reconstituting the solution due to their physical condition or a caregiver, such as a family member, has to locate the lyophilized powder and diluent in order to prepare the formulation for administration.

B. Suspensions

To prepare suspensions, the peptide, e.g., glucagon is typically micronized with one or more humectants to increase the rate of dissolution upon administration. The peptide can be micronized with one or more salts, such as sodium chloride, sugars, such as trehalose, one or more water-soluble polymers, or combinations thereof. The peptide can be micronized using techniques known in the art, such as phase inversion, frozen emulsion, and spray drying.

Spray drying includes the steps of atomization of a solution containing one or more solid (e.g., therapeutic agent) via a nozzle spinning disk, or other device, followed by evaporation of the solvent from the droplets. The nature of the powder that results the function of several variables including the initial solute concentration, size distribution of droplets produced and the rate of solute removal. The particles produced may contain aggregates of primary particles that consist of crystals and/or amorphous solids depending on the rate and conditions of solvent removal.

Spray-drying processes for preparing ultra-fine powders of biological macromolecules such as proteins, oligopeptides, high molecular weight polysaccharides, and nucleic acids are described in U.S. Pat. No. 6,051,256. Freeze-drying procedures are well known in the art, and described, for example, in U.S. Pat. No. 4,608,764 and U.S. Pat. No. 4,848,094. Spray-freeze-drying processes are described in U.S. Pat. No. 5,208,998. Other spray-drying techniques are described, for example, in U.S. Pat. Nos. 6,253,463; 6,001,336; 5,260,306; and International Patent Publication Nos. WO 91/16882 and WO 96/09814.

The micronized drug can be suspended in an appropriate carrier, such as low-molecular weight polyethylene glycol, prior to use.

IV. Methods of Use

Glucagon is a peptide hormone secreted by the alpha cells of the pancreas that naturally triggers the conversion of glycogen to glucose in hepatocytes via glucagon receptors. Glucagon also stimulates gluconeogenesis, the generation of glucose from metabolic precursors. Both of these actions serve to raise blood glucose levels as the countervailing peptide hormone to insulin.

The solutions and suspensions described herein can be used to treat patients who require rescue from severe diabetic hypoglycemia. The formulations can be administered parenterally via syringe or other appropriate device, such as a pen injection device or auto-injection device.

The solutions described herein are stable to thermal degradation (e.g., aggregation) over a period of about 30 days; therefore, the solutions can be stored in a syringe and can be administered as soon as necessary. The improved stability at elevated temperatures allows the patient to keep the pre-loaded syringe on their person for rapid administration if necessary.

The glucagon does not have to be reconstituted prior to administration, as is necessary for currently commercially available formulations. This decreases the time of administration and avoids the necessity of reconstitution, which can be difficult if required to be done by the patient suffering from severe diabetic hypoglycemia or a family member who must first locate the lyophilized power and delivery vehicle and who may be distressed by the patient's severe condition, e.g., diabetic coma.

The formulations described herein can be administered to any diabetic patient (type I and type II) who would benefit from a bi-hormonal (glucagon and insulin) pump. To the use in a pump, pump cartridges can be pre-filled with the solution or suspension. Because the solutions/suspensions have improved stability at higher temperatures, such as body temperature, the cartridges can be carried by the person on the person.

Glucagon can also be used in cases of nesidioblastosis and insulinoma, when the beta cells of the pancreas secrete an excess of insulin into circulation.

EXAMPLES

Example 1. Stability of Glucagon Formulations

Materials and Methods

A series of formulations containing glucagon dissolved in glycerin were prepared. The formulations are described in Table 1.

TABLE 1

Descriptions of glucagon formulations

| Formulation | Glycerin | Arginine | PER 977 | trehalose | Sodium Bicarbonate |
|---|---|---|---|---|---|
| Formulation 1 | x | | | | |
| Formulation 2 | x | x | | | |

TABLE 1-continued

Descriptions of glucagon formulations

| Formulation | Glycerin | Arginine | PER 977 | trehalose | Sodium Bicarbonate |
|---|---|---|---|---|---|
| Formulation 3 | x | | x | | |
| Formulation 4 | x | | x | x | x |

The stability of the formulations in Table 1 was measured at 40° C., while the formulations were agitated using an end-over-end stirrer.

Results

The results are shown in FIG. 1. The peak area of the glucagon peak, as measured by HPLC, decreased almost 80% over about 6 days for glucagon dissolved in glycerin only. In contrast, for glucagon dissolved in glycerin and containing arginine, PER 977, or PER 977, sodium bicarbonate, and trehalose, the formulations showed no decrease in the peak area over 6 days. At day 13, the formulations containing PER 977 and PER 977, sodium bicarbonate, and trehalose has exhibited the same peak area, while the formulation containing arginine showed approximately a 10% decrease in peak area. At day 20, the formulation containing arginine showed approximately a 15% decrease in peak area, while the decrease in the peak area for the PER 977 formulation and PER 977, sodium bicarbonate, and trehalose was negligible, 1-2% and 0%, respectively. At day 28, the formulation containing arginine showed approximately a 20% decrease in peak area, while the decrease in the peak area for the PER 977 formulation and PER 977, sodium bicarbonate, and trehalose was 10% and 1-2%, respectively.

Example 2. Alternative Glucagon Formulation

A formulation having the following composition was prepared:

| Solvent | Excipient 1 | Excipient 2 | Excipient 3 | Excipient 4 | Glucagon |
|---|---|---|---|---|---|
| Glycerol | PER977 (10 mg/mL) | NaHCO3 (10 mg/mL) | Sucrose (10 mg/mL) | m-cresol (2 mg/mL) | 1 mg/mL |

Figure 2:
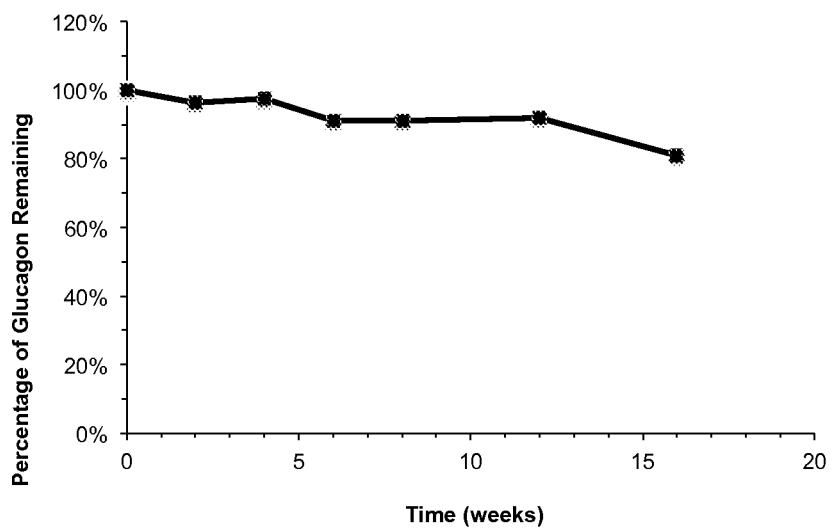
FIG. 2 is a graph showing the reduction in peak area of the glucagon peak as measured by HPLC as a function of time (weeks) for glucagon dissolved in glycerin with a di-arginine piperazine, trehalose, sodium bicarbonate and m-cresol (■), when stored at 40° C.

PER977 and sucrose were dried in a vacuum oven at 55° C. for 3 days. Sodium bicarbonate was dried in vacuum oven at room temperature for 3 days. Sodium bicarbonate, sucrose and PER977 were weighed in a 5 mL glass vial. Glycerol was added to the vial. The vial was purged with argon and closed with a crimp top in a glove box, and kept in a 55° C. incubator on a shaker until all the excipients dissolved. It took about 3 to 4 days depending on the total volume of the formulation. After all the excipients dissolved, 2 mg/mL of m-cresol and 1 mg/mL of glucagon was added in the vial. The vial was purged with argon and closed with a crimp top in a glove box, and placed on a shaker at room temperature until the glucagon dissolved, about 24 hours. Percent glucagon remaining as a function of time for this formulation when stored at 40° C. is plotted in FIG. 2.

We claim:

1. A stabilized glucagon formulation comprising glucagon dissolved in glycerin, wherein the formulation contains less than 5%, 1%, 0.5%, 0.25%, 0.1%, or 0.05%, weight by volume of water and an effective amount of a di-arginine piperazine to increase the stability of the glucagon.

2. The formulation of claim 1, wherein the concentration of glucagon is from about 1.0 mg/ml of glucagon to about 10 mg/ml of glucagon.

3. The formulation of claim 2, wherein the concentration of glucagon is about 1 mg/ml.

4. The formulation of claim 2, wherein the concentration of glucagon is about 5 mg/mi.

5. The formulation of claim 1, wherein the di-arginine piperazine has the formula:

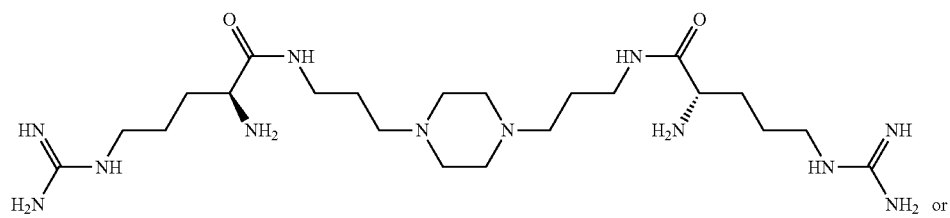

2-Amino-5-guanidino-pentanoic acid (3-{4-[3-(2-amino-5-guanidino-pentanoylamino)-propyl]-piperazin-1-yl}-propyl)-amide

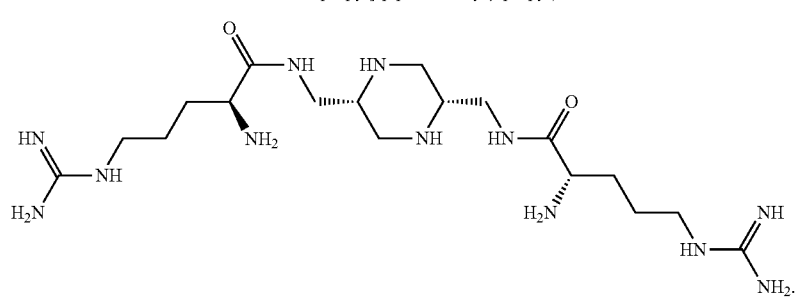

2-Amino-5-guanidino-pentanoic acid {5-[(2-amino-5-guanidino-pentanoylamino)-methyl]-piperazin-2-ylmethyl}-amide 6. The formulation of claim 5, wherein the concentration of the di-arginine piperazine is from about 5 mg/ml of di-arginine piperazine to about 100 mg/ml of di-arginine piperazine.

7. The formulation of claim 6, wherein the concentration of the di-arginine piperazine is about 10 mg/ml.

8. The formulation of claim 6, wherein the concentration of the di-arginine piperazine is about 20 mg/ml.

9. The formulation of claim 1 wherein the formulation is a solution, wherein the solution further comprises a pH-altering agent.

10. The formulation of claim 9, wherein the pH-altering agent is sodium bicarbonate.

11. The formulation of claim 10, wherein the pH of the formulation is adjusted to between 7 and 8.5.

12. The formulation of claim 10, wherein the pH of the formulation is adjusted to between 8 and 8.5.

13. The formulation of claim 10, wherein the concentration of sodium bicarbonate is from about 5 mg/ml of sodium bicarbonate to about 20 mg/ml of sodium bicarbonate.

14. The formulation of claim 10, wherein the concentration of sodium bicarbonate is about 10 mg/mi.

15. The formulation of claim 10, wherein the concentration of sodium bicarbonate is about 20 mg/ml.

16. The formulation of claim 1, wherein the formulation further comprises a sugar.

17. The formulation of claim 16, wherein the sugar is a disaccharide.

18. The formulation of claim 17, wherein the disaccharide is sucrose.

19. The formulation of claim 18, wherein the concentration of sucrose is from about 5 mg/ml of sucrose to about 15 mg/ml of sucrose.

20. The formulation of claim 18, wherein the concentration of sucrose is about 10 mg/ml.

21. The formulation of claim 17, wherein the disaccharide is trehalose.

22. The formulation of claim 21, wherein the concentration of trehalose is from about 5 mg/ml of trehalose to about 15 mg/ml of trehalose.

23. The formulation of claim 22, wherein the concentration of trehalose is about 10 mg/ml.

24. The formulation of claim 1, wherein the formulation further comprises an antimicrobial agent.

25. The formulation of claim 24, wherein the antimicrobial agent is metacresol (m-cresol).

26. The formulation of claim 25, wherein the concentration of m-cresol is from about 0.5 mg/ml of m-cresol to about 3.0 mg/ml of m-cresol.

27. The formulation of claim 26, wherein the concentration of m-cresol is about 1.5 mg/ml.

28. The formulation of claim 26, wherein the concentration of m-cresol is about 2 mg/ml.

29. The formulation of claim 1, wherein the formulation further comprises a non-aqueous cosolvent.

30. The formulation of claim 29, wherein the non-aqueous cosolvent is ethanol.

31. The formulation of claim 30, wherein the concentration of ethanol is from about 1 to about 50.

32. The formulation of claim 30, wherein the concentration of ethanol is from about 10 to about 40 volume percent.

33. The formulation of claim 30, wherein the concentration of ethanol is from about 20 to about 30 volume percent.

34. A unit dosage form comprising the stabilized glucagon formulation of claim 1.

35. The unit dosage form of claim 34, wherein the dosage form is a syringe or a cartridge.

36. A method of treating diabetes or hypoglycemia in a patient in need thereof comprising administering a stabilized glucagon formulation comprising a glucagon dissolved in glycerin, wherein the formulation contains less than 5%, 1%, 0.5%, 0.25%, 0.1%, or 0.05%, weight by volume of water, and an effective amount of a di-arginine piperazine to increase the stability of the glucagon.

* * * * *

UNITED STATES PATENT AND TRADEMARK OFFICE
CERTIFICATE OF CORRECTION

PATENT NO. : 9,956,287 B2  
APPLICATION NO. : 14/766347  
DATED : May 1, 2018  
INVENTOR(S) : Sasha H. Bakhru et al.

Page 1 of 1

It is certified that error appears in the above-identified patent and that said Letters Patent is hereby corrected as shown below:

In the Specification

Column 7, Line 4, please replace "1 mg/mL glycerin", with "1 mg/mL glucagon".

Column 7, Lines 29-30, please replace "solvents, and
   DMSO can be prepared", with "solvents, and DMSO can be prepared".

Column 7, Line 36, please replace "thereof "Low-molecular Weight",", with "thereof. "Low-molecular weight",".

Column 9, Line 49, please replace "thereof "Low-molecular weight",", with "thereof. "Low-molecular weight",".

Column 11, Line 53, please replace "that results the function of", with "that results is the function of".

Column 12, Line 39, please replace "To the use", with "For Use".

In the Claims

Claim 4, Column 14, Line 36, please replace "about 5 mg/mi", with "about 5 mg/ml".

Claim 14, Column 15, Line 23, please replace "about 10 mg/mi", with "about 10mg/ml".

Signed and Sealed this  
Thirtieth Day of October, 2018

Andrei Iancu  
*Director of the United States Patent and Trademark Office*